United States Patent [19]

Gargani

[11] 4,346,234
[45] Aug. 24, 1982

[54] PROCESS FOR THE PREPARATION OF THE SODIUM SALT OF MERCAPTOPROPIONYLGLYCINE

[76] Inventor: Pietro Gargani, Via Ripamonti, 166-Milano, Italy

[21] Appl. No.: 145,007

[22] Filed: Apr. 29, 1980

Related U.S. Application Data

[63] Continuation-in-part of Ser. No. 45,827, Jun. 5, 1979, abandoned.

[30] Foreign Application Priority Data

Jun. 16, 1978 [IT] Italy ............................. 24637 A/78

[51] Int. Cl.³ .......................................... C07C 149/243
[52] U.S. Cl. .................................... 562/556; 424/319
[58] Field of Search ............................... 562/556

[56] References Cited

U.S. PATENT DOCUMENTS

| | | | |
|---|---|---|---|
| 3,857,951 | 12/1974 | Buret | 424/319 |
| 3,897,480 | 7/1975 | Mita | 562/556 |
| 3,971,828 | 7/1976 | Mita | 562/556 |
| 4,108,886 | 8/1978 | Ondetti | 562/556 |

FOREIGN PATENT DOCUMENTS

| | | | |
|---|---|---|---|
| 2349707 | 4/1974 | Fed. Rep. of Germany | 562/556 |
| 39-5464 | 4/1964 | Japan | 562/556 |
| 39-11616 | 6/1964 | Japan | 562/556 |
| 1023003 | 3/1966 | United Kingdom | 562/556 |

*Primary Examiner*—Natalie Trousof
*Assistant Examiner*—Michael Shippen
*Attorney, Agent, or Firm*—Morgan, Finnegan, Pine, Foley & Lee

[57] ABSTRACT

Sodium salt of mercaptopropionylglycine of formula:

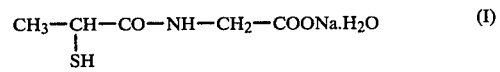

(I)

This salt is prepared by reacting 2-mercaptopropionylglycine with sodium-2-ethylhexanoate.

It is a very active protector of the hepatic cell and it can be also efficaciously used as a mucolytic agent by inhalation or in the form of suppositories.

2 Claims, No Drawings

PROCESS FOR THE PREPARATION OF THE SODIUM SALT OF MERCAPTOPROPIONYLGLYCINE

This application is a continuation-in-part of application Ser. No. 045,827, filed June 5, 1979, now abandoned.

This invention relates to the sodium salt of mercaptopropionylglycine of formula:

$$CH_3-CH(SH)-CO-NH-CH_2-COONa \cdot H_2O \quad (I)$$

to an industrially valid process for its preparation, and to therapeutic compositions which contain it as their active principle.

Mercaptopropionylglycine $$CH_3-CH(SH)-CO-NH-CH_2-COOH$$

is a compound which has been known for some years, and has found considerable use as a hepatoprotector and as an antidote in mercury, arsenic and drug poisoning.

This compound, which has a pH of around 1.6, is administered either parenterally in a buffer solution, or orally as such, in the form of a syrup or tablets.

Mercaptopropionylglycine, wether in buffer solution or as such, has a limited stability with time, this being of the order of a few months and variable according to the temperature and humidity environmental conditions.

It has now been discovered, and this forms the object of the present invention, that it is possible to industrially prepare the solid crystalline monohydrate sodium salt of mercaptopropionylglycine of formula (I), and that once this salt has been isolated and dried, it is stable for a practically indefinite time under any climatic conditions.

Sodium mercaptopropionylglycinate can be made into a solution at any time, simply by diluting with water without adding buffer agents and/or stabilisers.

In addition its substantially neutral pH, which lies between 5.2 and 7.2, allows it to be administered orally, by inhalation or by suppositories, and therefore enables it to be used in fields never before attempted by the corresponding acid, because of its strongly acid pH.

It has thus been found for example that besides being a very active hepatoprotector, the sodium salt can also be effectively used as a mucolithic by inhalation or as suppositories.

The preparation of the sodium salt of an organic acid would seem to be a problem which is immediately solved using the normal methods of neutralising the acid with a base.

However, it has been surprisingly found (and this probably explains why up to the present time only the free acid has been used, in spite of its drawbacks) that it is practically impossible to obtain sodium mercaptopropionylglycinate from the acid in a solid crystalline state with acceptable yields if it is isolated by neutralising with an alkaline base such as NaOH, $Na_2CO_3$ or $NaHCO_3$. Numerous tests have been carried out with said bases in aqueous solution and in alcoholic solution, but have given no formation of product.

Other tests conducted with more common sodium alcholates, such as methyl alcoholate, ethyl alcoholate and isopropyl alcoholate have given only very low yields of a product which is difficult to purify.

It has now been surprisingly found that sodium mercaptopropionylglycinate can be prepared industrially, with practically quantitative yields, by reacting 2-mercaptopropionylglycine with sodium 2-ethylhexanoate in isobutanol, in accordance with the equation $$CH_3-CH(SH)-CO-NH-CH_2-COOH +$$

$$CH_3(CH_2)_3-CH(C_2H_5)-CH_2-ONa \longrightarrow$$

$$CH_3-CH(SH)-CO-NH-CH_2-COONa +$$

$$CH_3-(CH_2)_3-CH(C_2H_5)-CH_2OH$$

The reaction is carried out at a temperature of 20° to 25° C.: precipitation is induced and completed by cooling to 10°–15° C. for some hours and by adding water in nearly stoichiometric amount with respect to mercaptopropionylglycine. The salt is separated by filtration or centrifuging.

Fresh mercaptopropionylglycine is added to the isobutanol solution, which contains a small percentage of unconverted mercaptopropionylglycine, and the solution is recycled. It can therefore be said that the yield of the sodium salt with respect to the converted product is quantitative.

Salification tests conducted with sodium 2-ethylhexanoate in solvents other than isobutanol, such as ethylacetate, have given distinctly lower yields. Mercaptopropionylglycine, which is the starting substance for the preparation of the sodium salt according to the invention, is prepared by known methods (U.S. Pat. No. 3,246,025).

The following example gives all the operational details for preparing the product according to the present invention.

EXAMPLE 27 kg of soda in the form of flakes and 50.3 kg of glycocoll are dissolved in 331 kg of water, cooling with brine to −6° C.

229 kg of iced water, 34 kg of soda in the form of flakes and 149 kg of alphabromopropionylbromide are gradually added to this solution in such a manner that the solution always remains basic, and its temperature does not exceed 0° C.

About 12 hours are generally necessary to add all the mixture.

It is left for half an hour for the reaction to complete, and 88 kg of thiobenzonic acid are then slowly added, cooling if necessary, so that the temperature does not exceed 25° C.

The mixture is left to react for one night, and is then acidified with $H_2SO_4$ to a pH of 1.

The precipitate which is formed is separated by centrifuging, and is washed firstly with water and then with ethylacetate.

370 kg of alphathiobenzoylpropionylglycine are added to a reactor containing 200 liters of water and 137 kg of sodium bicarbonate.

The mixture is left to react for some hours, and when the temperature of the mass begins to fall, 85 kg of gaseous ammonia are bubbled through. The mixture is left overnight at 30° C., and the benzamide which is formed is then filtered off.

The mother liquor is acidified with 96% $H_2SO_4$ to a pH of 1.6–1.7, and after leaving for a few hours, 500 kg of precipitated crude alphamercaptopropionylglycine are separated.

The product is purified by adding it to a mixture of 1000 liters of ethylacetate, 400 liters of chloroform and 500 liters of acetone, filtering off the precipitate of residual salts.

The mixture of solvents is removed under vacuum, and the oily residue is crystallised by chloroform.

100 kg of mercaptopropionylglycine are suspended in 625 liters of isobutanol at 20°–25° C., and a solution of 103 kg of sodium 2-ethylhexanoate in 430 liters of isobutanol is added.

The mixture is agitated for 30 minutes at ambient temperature, and is then cooled for 3 hours to 10°–15° C.

After this time Kg 10.7 of water are added, the precipitate is filtered off, is washed with isobutanol and then with acetone, and is dried.

104 kg of sodium mercaptopropionylglycinate monohydrate are obtained.

100 kg of mercaptopropionylglycine are added to the isobutanol mother liquor, and this is recycled.

The characteristics of the pure product, which is in the form of a white crystalline powder, are as follows:

Elementary analysis referred to the anhydrous product: C%=32.42; H%=4,35; N%=7.56; S%=17.31; corresponding to the formula $C_5H_8NO_3SNa$.

M.W.=203.2.

pH between 5.2 and 7.2 in a 1% aqueous solution.

M.P.=82°–88°—loss of water of crystallisation; 155°–160° C.—complete fusion.

What we claim is:

1. A process for preparing sodium 2-mercaptopropionylglycinate monohydrate of formula:

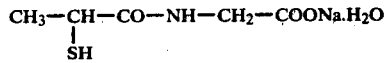

wherein 2-mercaptopropionylglycine is reacted with sodium 2-ethylhexanoate in an anhydrous mean, at ambient temperature and the formed salt is precipitated by cooling and addition of water.

2. A process as claimed in claim 1, wherein the reaction is carried out at ambient temperature in isobutanol, and the salt is precipitated by cooling to 10°–15° C., and addition of water in nearly stoichiometric amount with respect to mercaptopropionylglycine.

* * * * *